(12) United States Patent
Wu et al.

(10) Patent No.: US 8,808,977 B2
(45) Date of Patent: Aug. 19, 2014

(54) METHOD OF INACTIVATING VIRUS IN CIRCULAR BLOOD AND ITS APPLICATIONS IN TREATING VIRAL DISEASES

(75) Inventors: Weixing Wu, Beijing (CN); Yuen Kam, Beijing (CN)

(73) Assignee: Beijing Jingjing Medical Equipment Co., Ltd, Beijing (CN)

( * ) Notice: Subject to any disclaimer, the term of this patent is extended or adjusted under 35 U.S.C. 154(b) by 2456 days.

(21) Appl. No.: 10/551,334

(22) PCT Filed: May 21, 2004

(86) PCT No.: PCT/CN2004/000516
§ 371 (c)(1),
(2), (4) Date: Apr. 3, 2007

(87) PCT Pub. No.: WO2004/103443
PCT Pub. Date: Dec. 2, 2004

(65) Prior Publication Data
US 2007/0178436 A1    Aug. 2, 2007

(30) Foreign Application Priority Data

May 22, 2003   (CN) .............................. 2003 1 36647

(51) Int. Cl.
| | | |
|---|---|---|
| *A61L 2/10* | (2006.01) | |
| *A01N 1/02* | (2006.01) | |
| *C12M 3/06* | (2006.01) | |
| C12M 1/00 | (2006.01) | |
| A61M 31/00 | (2006.01) | |

(52) U.S. Cl.
USPC ...... 435/2; 435/283.1; 435/286.5; 435/292.1; 435/297.1; 604/4.01; 604/5.01; 604/5.02; 604/6.08; 604/6.09; 604/7; 604/20; 607/1

(58) Field of Classification Search
None
See application file for complete search history.

(56) References Cited

U.S. PATENT DOCUMENTS 3,223,642 A * 12/1965 Smith et al. .................. 252/78.3
3,677,667 A *  7/1972 Morrison ...................... 417/474

(Continued)

FOREIGN PATENT DOCUMENTS

| CN | 1249952 A | 4/2000 |
|---|---|---|
| JP | 2002/245832 | 9/2000 |
| WO | WO 00/59551 A1 | 10/2000 |

OTHER PUBLICATIONS

Prahl, S. "Optical Absorption of Methylene Blue" Oregon Medical Laser Center <URL:http://omlc.ogi.edu/spectra/mb/index.html> accessed Jul. 12, 2010; archived online Jul. 14, 2001, 3 pages.*

(Continued)

*Primary Examiner* — Jon P Weber
*Assistant Examiner* — Aaron J Kosar
(74) *Attorney, Agent, or Firm* — Amin, Turocy & Watson, LLP (57) ABSTRACT

The present invention relates to a method for illuminating the viruses in a circulatory blood, comprising the following steps of: 1) Adding an anticoagulant into a whole blood source and establishing a circulation system for the whole blood source; 2) Withdrawing the whole blood with the anticoagulant into a plasma-separating device for a separation, when finished, directly pumping the red-blood cells back into the whole blood source and transporting the plasma into a mixing transport pump after the separation; 3) Meanwhile, pumping a photosensitizer methylene blue into the mixing transport pump so that the methylene blue is mixed with the plasma and pumped together into a plasma container; 4) Using an illumination device to illuminate the plasma in the plasma container for virus illumination, and pumping the virus-illuminated plasma into a removing device for removing off the photosensitizer; 5) The methylene blue being absorbed by the removing device and the plasma illuminated being transfused back into the whole blood system; 6) Repeating the step 2 to the step 5 until the virus content in the whole blood source is reduced by 99.99%. The present invention can process blood in a batch, as a pipeline, and can utilize aseptic and disposable sealed systems isolated from the outside environment for processing. The processed plasma flows back into the whole blood source and can be directly transfused into the human body. Still, the invention may be further used to treat virus-diseases such as Hepatitis B, Hepatitis C, AIDS and etc., and to eliminate the viruses of organ transplantation recipient.

8 Claims, 4 Drawing Sheets

(56) References Cited

U.S. PATENT DOCUMENTS

| | | | |
|---|---|---|---|
| 3,989,740 A | * | 11/1976 | Broussard et al. ............ 560/224 |
| 5,304,113 A | | 4/1994 | Sieber et al. ................... 604/4 |
| 5,516,629 A | * | 5/1996 | Park et al. ...................... 435/2 |
| 5,935,092 A | | 8/1999 | Sun et al. ........................ 604/4 |
| 6,177,403 B1 | * | 1/2001 | Stedman ......................... 514/2 |

OTHER PUBLICATIONS

Sikurová, L., et al, "Penetration of Laser Light through Blood Derivatives", Laser Physics, 2003, 13(2), pp. 217-221.*

Fantini, S. et al "Quantitative Determination of the Absorption Spectra of Chromophores in Strongly Scattering Media: A Light-Emitting-Diode Based Technique" Applied Optics, 1994, 33(22), pp. 5204-5213.*

Corash, L. "Inactivation of Infectious Pathogens in Labile Blood Components: Meeting the Challenge" Transfus.Clin.Biol. Jun. 2001,8(3), pp. 138-45.*

World Health Organization, "Annex 4: Guidelines on Viral Inactivation and Removal Procedures Intended to Assure the Viral Safety of Human Blood Plasma Products" WHO Technical Report, Series No. 924, 2004, pp. 150-224.*

Schmidt, M.H. "Light-emitting Diodes as a Light Source for Intraoperative Photodynamic Therapy" Neurosurgery, Mar. 1996, 38(3), 552-557.*

* cited by examiner

METHOD OF INACTIVATING VIRUS IN CIRCULAR BLOOD AND ITS APPLICATIONS IN TREATING VIRAL DISEASES

FIELD OF THE INVENTION

The present invention relates to a processing method of purifying blood, particularly to a method to illuminate viruses in circulating blood.

BACKGROUND ART

It is well known that blood itself is fragile to be infected with viruses, such as Hepatitis B virus, Hepatitis C virus and HIV, and that transfusing blood is of danger to spread virus-diseases. Blood safety is a primary issue that affects health and safety of life. One of safeguards to protect the blood safety is illumination of viruses for blood and blood components. Methylene blue/photochemical process may be used for the illumination of viruses in human plasma and have obtained significant effects onto single bags of clinic plasma. However, the process used for processing a single bag of plasma has comparatively complicated steps: it needs to additionally add Methylene blue into the plasma under a specific environment and to encapsulate the bag prior to processing; then the plasma is placed into an illumination device to process; yet the processed plasma can not be used directly in transfusion until the bag containing plasma is reopened to eliminate the left methylene blue from the plasma and the plasma is remixed with red blood cells. Therefore, a highly cost operating environment is needed and the risk that blood within the bag is infected goes up because the bag is opened and sealed very often, the plasma is remixed with red blood cells. Apparently, such a method used to individually process single bags of plasma can not meet the requirement if purified blood needs to be supplied substantially and stably. So creating a method that can illuminate viruses for substantial blood is desirable.

On the other hand, while current treatments to virus diseases are generally taken the form of medical treatment, the curative effect becomes not apparent. Especially, for diseases such as chronical hepatitis, AIDS and SARS, etc., no efficient curative medicine is available so far, therefore, one thing is urgently needed, namely, to create a cure that might essentially exterminate the infective pathogen generating the diseases, thereby efficiently curing such diseases.

SUMMARY OF THE INVENTION

The purpose of the present invention is to provide a method of illuminating viruses in the circulating blood, which recurrently processes the blood on-line and can meet the requirement to real-time & on-line illuminate the viruses in the circulating blood.

To fulfill the above-mentioned aim, the present invention takes the following design. A method of illuminating the viruses in circulating blood includes the steps of:

1) Adding an anticoagulant into a whole blood source and establishing a circulation system for the whole blood source;
2) Withdrawing the whole blood with the anticoagulant into a plasma-separating device for a separation, when finished, directly pumping the red-blood cells back into the whole blood source and transporting the plasma into a mixing transport pump after the separation;
3) Meanwhile, pumping a photosensitizer methylene blue into the mixing transport pump so that the methylene blue is mixed with the plasma and pumped together into a plasma container;
4) Using an illumination device to illuminate the plasma in the plasma container for virus illumination, then pumping the virus-illuminated plasma into a removing device;
5) The methylene blue being absorbed by the removing device for removing off the photosensitizer and withdrawing the illuminated plasma back into the whole blood source;
6) Repeating the step 2 to the step 5 until the virus load in the whole blood system is reduced by 99.99%.

Wherein, the whole blood is a reserve blood from a blood station, a blood bank, a blood bag or a blood storage device, or a circulating blood from a tube of blood transfusion.

The mixing transport pump is a peristaltic pump, which transfers the plasma at the speed of 30 to 150 ml per minute, and transfers the photosensitizer 100 times slower.

The light source in the illumination unit is a set of LEDs. The time of illumination given by the light source of the illumination unit to the plasma flowing into the plasma container is 60 seconds. The plasma container is a sealed container having two conduits at each side.

An adsorbent used in the device for removing off the photosensitizer is Attapulgite.

The above-mentioned pump conduit, tube, plasma separator, and plasma container all are aseptic and are disposable sealed systems isolated from the outside environment.

Through this method, purified plasma is obtained and may be directly back to the whole blood to transfer into the human body. Since the complicated processing for the illumination of virus is simplified, blood processing can be implemented in a batch, as a pipeline, during blood circulation so that a real-time online illumination of virus is realized to the plasma. Additionally, the safety of the blood is guaranteed through using the aseptic and disposable sealed systems to process the blood.

Another purpose of the present invention is to apply the aforementioned method for illumination of virus in the extracorporeal circulation blood to the illumination of virus in circulation and the treatments to virus diseases.

The procedure of the treatment includes: establishing an extracorporeal circulation for patient, using a blood component separator to separate the blood of the patient into plasma and red blood cell (erythrocyte), etc., adding a specific amount of photosensitizer into the plasma, removing the photosensitizer after illuminating by an illumination unit, mixing the processed plasma with the previously separated red blood cell and other components as well, then transfusing the mixed blood back into the body of the patient.

The present invention applies to the process of blood purification. As a measure to treat the disease, the method implements an illumination to infective pathogen of patient's body in dynamic circulating blood. The amount of virus in patient's body can be effectively decreased after specific times of the circulation, thus improving the treatment effect.

DETAILED DESCRIPTION OF THE PREFERRED EMBODIMENTS

Figure 1:
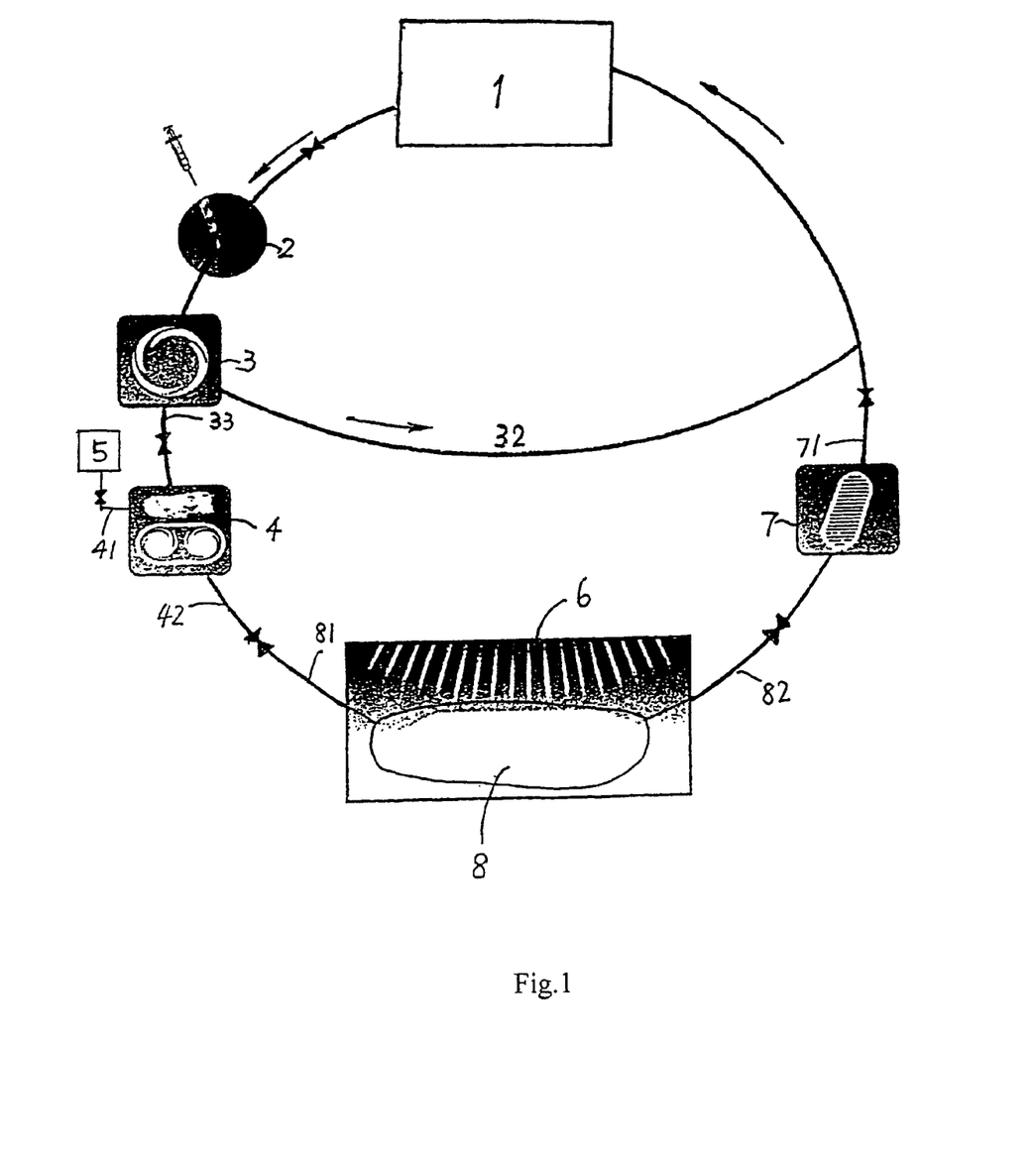
FIG. 1 is a processing chart of the method of the present invention.

A processing flowchart of the method for illumination of virus in circulating blood of the present invention is shown in FIG. 1, which includes the steps of:

1) Adding an anticoagulant into a whole blood 1, and establishing a whole blood circulation system.

2) Pumping the whole blood with the anticoagulant into a centrifuge 3, separating the whole blood and pumping the blood-cell directly back into the whole blood 1, and transferring the plasma into a mixing transport pump 4 via a plasma transportation tube33.

3) at the same time, adding photosensitizer methylene blue into the mixing transport pump 4 via a photosensitizer transportation tube41, adjusting the speed and ratio of the adding so that the methylene blue and the plasma are mixed in a outflow tube42 of the mixing transport pump 4.

4) using an illumination unit 6 to perform illumination to the mixed plasma for the illumination of virus, after the illumination, pumping the plasma into a device 7 which is used to remove off the photosensitizer.

5) In the device 7 for removing off the photosensitizer, the methylene blue being absorbed, then pumping the plasma back to the whole blood 1 via a plasma output tube71.

So far, one circle of processing the whole blood 1 composing of separating the plasma, illuminating the virus and removing the photosensitizer is completed. At the moment, the virus in the plasma is reduced by 99.99%. The loop from step 2 to step 5 may be repeated for multiple times to process the whole blood until the virus level in the whole blood is not enough to affect body's health and formal functions of blood.

In the above process, the devices, equipments, reagents, and materials that are used include:

1) a whole blood: which may be reserve blood from a blood station, a blood bank, a blood bag or a blood storage device, or a circulating blood from a tube used for blood transfusion.

2) a plasma separating device: which may be a type of plasma separator manufactured by Beijing Jing Jing Medical Equipment Co.

3) a mixing transport pump: which may be a BT00-100M peristaltic pump manufactured by Baoding Longer Precision Pump Corp., Ltd 4) a light source used for the illumination unit: which may be a rectangular LED (600-700 nm of wavelength) that has processed into an illuminating plate. In the present invention, two such illuminating plates are placed to illuminate the plasma both from the upside and the downside together.

6) a method measuring the illumination of the illumination unit: which uses a luminometer to measure the strength of the illumination. The distance between measuring points and the distance between processing samples are the same.

7) a plasma container for the illumination unit: which may be a transparent blood bag (of 100 ml or 200 ml, made of PVC material).

8) an anticoagulant: which may be a CPDA (Citrate Phosphate Dextrose Adenin) solution, or an ACD (Anticoagulant-Citrate-Dextrose) Solution, or a heparin.

9) a photosensitizer methylene blue(MB): which may be a medicine of 20 mg/2ml for mainline manufactured by Beijing Yongkang pharmaceutical factory. The preparation for the methylene blue(MB): is conducted in an ultraclean workbench, one portion of methylene blue (MB) is diluted by 267.5 portions of 0.9% aseptic physiological saline to reconstitute a methylene blue storage solution of 100 μmol/L (containing 37.4 μg of methylene blue in each ml of solution). When the solution is used for illumination, it has to be diluted 100 times more, namely, the transporting speed of the methylene blue is 1 percent of the transporting speed of the plasma. The methylene blue solution is at the final concentration of 1.25 μg/ml.

10) an adsorbent material for absorbing the photosensitizer: which may be an attapulgite (a natural porous nanometer material), or an CAA(cross-linked agar beads entrapped attapulgite clay).

The process for preparing CAA includes:

A pre-processing of the attapulgite wherein, an attapulgite powder which is provided by Nanjing University pharmaceutical factory as a raw medicine is soaked in a dilute acid for about 2 hours before the powder neutralized by alkali; Distilled water is used to wash the powder until the powder is near neutral; The powder is dried at the temperature of 105° C. and then carefully crushed and sieved to distill the fine power under 100 mesh which can be used later.

The preparation of CAA and cross-linking reaction, wherein a proper amount of an agar powder, manufactured by Qingdao aquatic product processing factory, is placed into distilled water, so as to mix and suspend in the distilled water, the distilled water with the agar powder is then heated to boiling; the heating process might be finished only if the agar is melted and the solution has appeared half-lucid without jelly inside so that a agar solution with a concentration of 2 to 6 percent can be further formed; Moreover, the hot agar solution is mixed with some of the attapulgite powder occupying an 20 to 30% of the total mixture in weight; upon the mixture being stirred well, a pressured bead blasting is implemented to eject the said mixture into a pre-cooled medical paraffin oil mixture so that the size of the CAA can be best controlled to keep from blocking and coagulating; As a result, the agar beads entrapped attapulgite clay accumulated on the bottom of processing device can solidify into "soft beads" after cooling; These "soft beads" and the paraffin oil can be separated, and the left paraffin oil and the agar may be washed and removed by distilled water; every 100 ml of agar can obtain 200~250 mL of CAA.

Furthermore, the "soft beads" with other things including computerized quantity of cross-linked agent epoxy chloropropane (resteamed before use), diluted NaOH solution and suitable amount of stabilizer are put into a three-neck flask and mixed equally; The mixture is heated in hot water to generate cross-linking for 2 to 4 hours along with the incessant shaking of the mixture to prevent the soft beads from coagulating; When the cross-link reaction is finished, small amount of CAA is processed and washed clean by using distilled water so that the pH value of the CAA is near neutral; the CAA is then placed into a small flask and is heated to boiling for ten minutes; If there are no such phenomena as the distilled water is not transparent, the CAA is unclean or the agar falls off, then the cross-link reaction is finished and the CAA can be sterilized.

After cooling the above well-entrapped CAA, the CAA is filtered and washed by distilled water and neutralized by diluted acid; A special wash solution in removing epoxy Cross-linked agent may be added to soak the CAA; the CAA can be classified by a filtering sieve into the CAA with diameter smaller than 1 mm, the CAA with diameter between 1 and 2 mm and the CAA with diameter larger than 3 mm if no epoxy chloropropane exists by sampling and analyzing the CAA; those different classes of CAA are placed into bottles respectively, cleaned by ethanol and distilled water, soaked by distilled water and physiological saline, and sealed for use of sterilization later.

A process of sterilization wherein, the above CAA is sealed into the bottle and sterilized for 30 minutes at the temperature of 121° C.; The finished CAA can be gained for future use if no agar falls off after cooling and the solution is transparent.

Figure 2:
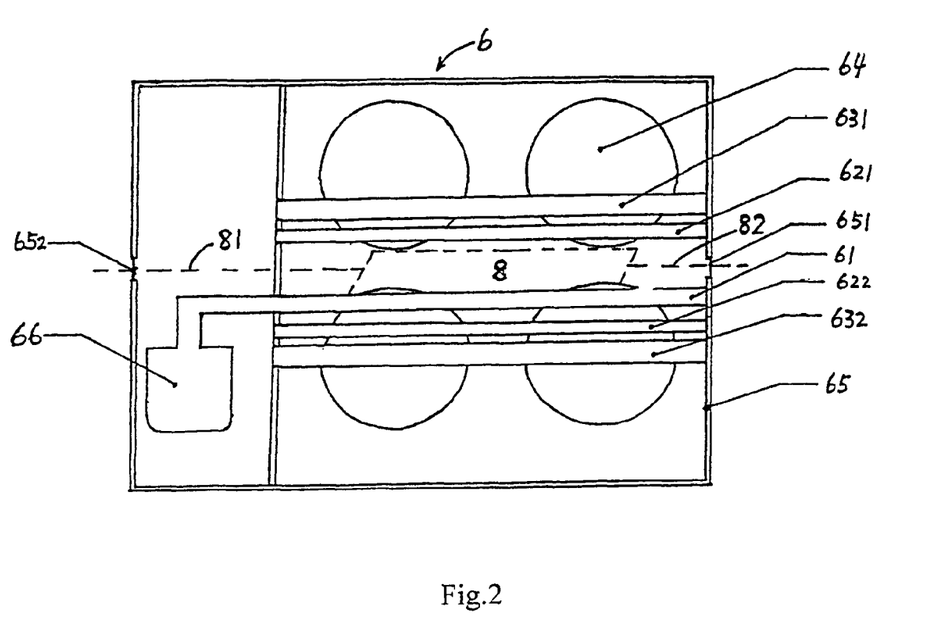
FIG. 2 is a schematic drawing of the illumination unit used in the method of the present invention.

In the present invention, a preferred illumination device 6 may have a structure as shown in the FIG. 2. The illumination device 6 includes a supporting plate 61 used to support a plasma container 8, two illuminating plates 621 and 622 used as the light sources respectively placed on the upside and on the downside of the supporting plate 61, two heat-sink plates 631 and 632 respectively arranged at the outside of each illuminating plate, and a fan set 64; The supporting device 61, the illuminating plates 621 and 622, the heat-sink plates 631 and 632, and the fan 64 are all disposed in a case 65 of the illumination device. The case 65 of the illumination device has a perforation 651 and 652 on each side, where an input blood tube 81 and an output blood tube 82 of the plasma container 8 which is disposed on the said supporting plate 61 respectively go through and reach out from the perforation 651 and the perforation 652 of the case 65 of the illumination device 6.

In the illumination device 6, the illumination plate 62 may be a LED set assembled by a plurality of LEDs, whose quantity and ways of arrangement are not uniform but are in accordance with the strength of illumination required.

The supporting device 61 is disposed in the case 65, on which the plasma container 8 is set, of the illumination device; a stepping motor 66 is set a one end of the supporting plate 61 in order that the plasma in the plasma container 8 can be further well-mixed with the methylene blue, passively the supporting plate 61 is shaken or trembled while the stepping motor is on operation.

An available plasma container 8 may be a sealed transparent container attached with a tube on its each end, or may be a plasma bag attached with a soft tube on its each end. The shape of the plasma container is preferably flat so as to guarantee the efficiency of virus illumination.

In the front of the illumination device 6, tubes are connected with a mixing transport pump 4. The pump 4 has two input ports, one is connected to a transport tube 33 for a plasma source and the other is connected to a transport tube 41 for a photosensitizer source 5; the output tube 42 of the pump 4 is directly connected to an input tube 81 of the plasma container 8. The pump 8 may pump the plasma and the photosensitizer at a specific speed and ratio to mix them in the output tube before the mixture is transported into the plasma container 8. The photosensitizer may be a methylene blue.

Figure 3:
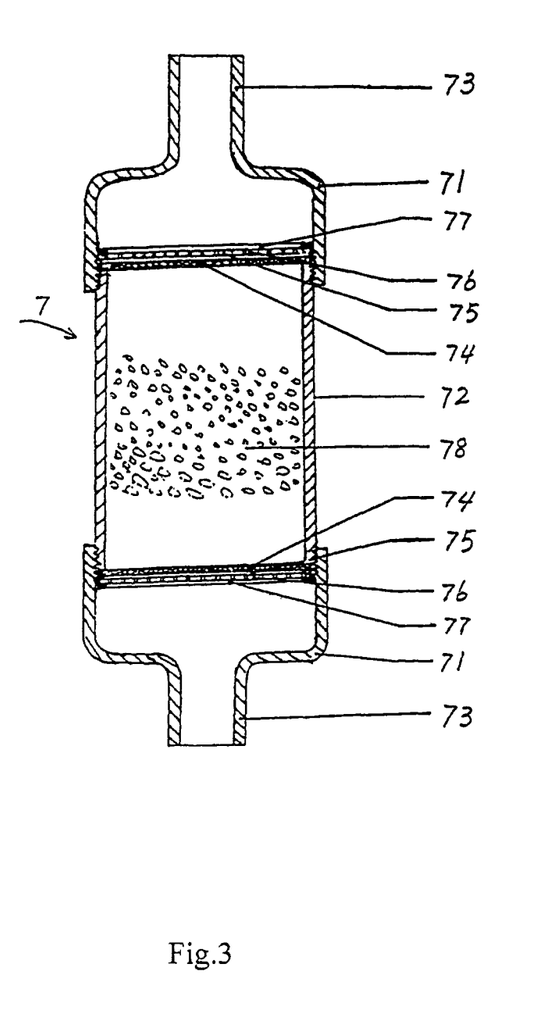
FIG. 3 is a schematic drawing of the device removing off the photosensitizer used in the method of the present invention.

In the present invention, a preferable photosensitizer-removing device 7 which is a device for filtering and absorbing the methylene blue may have a structure shown in the FIG. 3. From the FIG. 3, the device for filtering and absorbing 7 has an outer covering with a tube shape, including tube heads 71 at both ends and a middle part 72. The tube heads 71 and the middle part 72 are coupled by screwing them together. Each of the tube heads 71 has a connection end 73 extending out away from the tube head to connect with the tube. The diameter of the tube is 2 to 5 mm, but the diameter of the middle part 42 is 2 cm. Starting both ends of the middle part towards the outsides, a sponge layer 74, a non-woven cloth layer 75, a baffle 76 with holes and a ring-shape airproof gasket 77 are placed in turn. In the middle part 72, a adsorbent material 78 is filled, which is a natural porous nanometer material, namely, an attapulgite. These multi-layer structures at both sides of the middle part 72 permit liquid to infiltrate but separate the absorbent material 78 from entering the tube 73 at two sides of the device for filtering and absorbing 7. The airproof gasket 77 at the outer side of the baffle 76 may prevent the liquid in the middle part 72 from seeping out from the gaps between the middle part and the tube heads.

Figure 4:
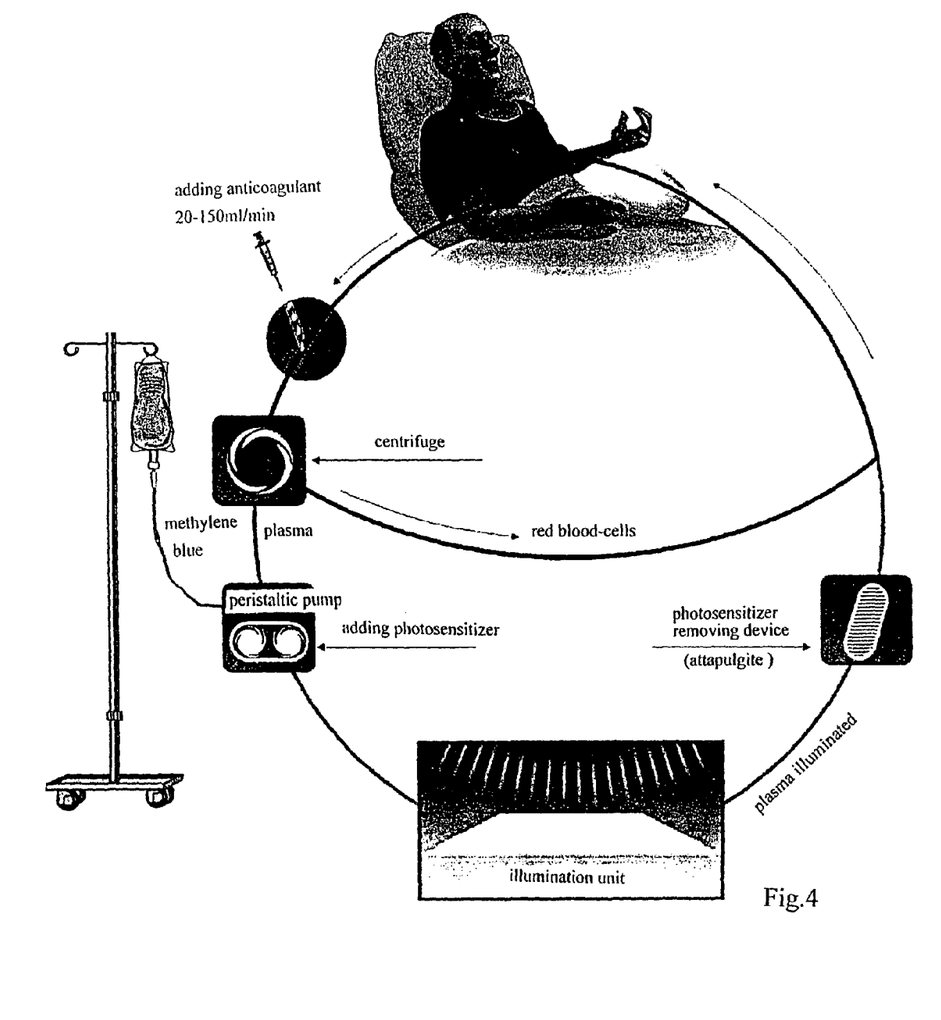
FIG. 4 is a processing chart of the method of the present invention when used to treat virus diseases.

The FIG. 4 shows when the method of the present invention is used for treatment, where, an ex vivo blood circulation of a patient is established first; A blood component separator is applied to separate the blood of the patient into plasma, red blood cells and other components; In the plasma, a specific amount of photosensitizer is added; and the photosensitizer is removed off after the plasma is illuminated by the illumination device; the processed plasma is remixed with the previously separated red blood cells and other components and is together transfused back into the body of the patient; the quantity of the virus in patient's body is effectively reduced after the circulation is conducted for some time, thereby obtaining the effect of treatment.

Embodiment One:

At the room temperature, 200 ml of ACD (Anticoagulant Citrate Dextrose) solution is added to 2000 ml of whole blood source taken from blood bags, as an anticoagulant; The mixed whole blood is withdrawn to a whole blood separating device at a speed of 100 ml/min; After the separation, while the red blood cells are pumped back into the whole blood, the plasma is transported into the peristaltic pump at a speed of 100 ml/min along with the addition of a 0.1 mmol/l methylene blue into the peristaltic pump at a speed of 1 ml/min; A mixed plasma and methylene blue then flows out from the peristaltic pump and is transported into a plasma container; the mixture is subject to 60 seconds of illumination by using a illumination device for illumination of viruses before the mixture flows into a device for removing off the photosensitizer; Next, a purified plasma having removed off the methylene blue once again flows back into the whole blood source; A controlling valve for the output tube of the whole blood source will be closed after the circulation lasts for 120 minutes; all of the blood has flown back to the whole blood and the whole process is complete.

Embodiment Two:

The method of the embodiment two is the same as that in the embodiment one except that the amount of the whole blood source is changed to 1000 ml, the anticoagulant is 300 units of heparin, the speeds of separating blood and transporting plasma are adjusted to 30 ml/min, the speed of adding methylene blue is 0.3 ml/min, the circulation is controlled to last for 60 minutes.

Embodiment Three:

At the room temperature, 900 units of heparin is added to 3000 ml of whole blood source taken from blood bags, as an anticoagulant; The mixed whole blood is withdrawn to a whole blood separating device at a speed of 150 ml/min; After the separation, the red blood cells flows into storage bags for red blood cell, while the plasma is transported into the peristaltic pump at a speed of 150 ml/min along with the addition of a 0.1 mmol/l methylene blue into the peristaltic pump at a speed of 1.5 ml/min; A mixed plasma and methylene blue then flows out from the peristaltic pump and is transported into a plasma container; the mixture is subject to 60 seconds of illumination by using an illumination device for illumination of viruses before the mixture flows into a device for removing off the photosensitizer; Next, a purified plasma having removed off the methylene blue flows back into the plasma storage bags via tubes; A controlling valve for the output tube of the whole blood source will be closed in 20 minutes; The red blood cells stored in the storage bags for red blood cells and the plasma stored in the plasma storage bags may be used by mixing them together or may be used without mixing.

By sampling the whole blood subject to the above processes, the quantities of viruses and various bio-chemical indices in the whole blood source can be tested; Furthermore, if the indices prior to the illumination are used to compare with those indices, an effect of illumination and a biological safety can be evaluated.

1. Testing the effect of illumination of virus

The tests, for example, may be conducted to VSV (vesicular stomatitis virus) and to Sindbis virus (SV) separately. In order to test the effect of illumination of virus, Cercopithecus aethiops (Vero) cells and $BRK_{21}$, cells are separately used to test virus titer with respect to the trace cytopathic effect and lgTCID50 is calculated according to the Karber method. Some results are shown in the following table 1-1:

TABLE 1-1

The effect of illumination of virus shown by comparing the plasma before and after being processed by using the present invention

| Volume of blood (ml) | circulatory time (mins) | virus titer left VSV | lg TCID$_{50}$ Sindbis |
|---|---|---|---|
| 1000 | 60 | ≤−0.5 | ≤−0.05 |
| 2000 | 120 | ≤−0.5 | ≤−0.05 |
| virus comparison | | 5.75 | 5.75 |

According to the table 1-1, the virus in the whole blood source is illuminated after the method of the present invention is utilized to process the whole blood source for a period of time.

2. Testing the impact on the plasma components by the processing procedure of the invention Materials and Method:

A detection kit for clotting factor VIII, IX: is purchased from Chengdu Research Institute of Transfusion, and used in accordance with the methods on its description.

Testing bio-chemical indices: is implemented by using an imported automatic biochemistry analyzer.

Testing clotting factors: is implemented by using an imported automatic hemostasis analyzer.

Testing the pH value of the plasma: is implemented by using an imported pH meter.

Testing the left methylene blue in the plasma after illumination is implemented by using an imported ultraviolet-visible spectrophotometer in accordance with the method of absorbency test under the item of methylene blue in Chinese Pharmacopoeia.

Testing complement $C_3$: is implemented by using an agar single-difflusion plate from Bangding Corporation.

2.1 Testing the impact on the activity of clotting factor VIII: is implemented by using a detection kit for factor VIII manufactured by Chengdu Research Institute of Transfusion. The test involves three batches of samples subject to a circulatory processing for 60 minutes, each batch of samples include two bags of plasma. The results of the test are shown in the following table 2-1, which indicate the activity of the clotting factor VIII in the plasma has reduced slightly after the 60-minute of circulatory processing, however the range of decrease of the activity is less than 20 percent.

TABLE 2-1

The impact on the activity of clotting factor VIII of plasma by 60 minutes of circulatory processing

| Batch No. of samples | I | II | III |
|---|---|---|---|
| Processed samples | | | |
| Activity of factor VIII (%) | 101(90.4%) | 131.1(85.1%) | 117.6(83.7%) |
| Comparative samples | | | |
| Activity of factor VIII (%) | 111.7(100%) | 154.1(100%) | 140.5(100%) |

2.2 Testing the impact on the activity of clotting factor IX: is implemented by using a detection kit for factor IX manufactured by Chengdu Research Institute of Transfusion. The test involves three batches of samples subject to a circulatory processing for 60 minutes, each batch of samples include two bags of plasma. The results of the test are shown in the following table 2-2, which indicate the activity of the clotting factor IX in the plasma has reduced slightly after the 60-minute circulatory processing, however the range of decrease of the activity is about 10 percent.

TABLE 2-2

The impact on the activity of clotting factor IX of plasma by 60 minutes of circulatory processing

| Batch No. of samples | I | II | III |
|---|---|---|---|
| Processed samples | | | |
| Activity of factor IX (%) | 106.1(88.3%) | 125.2(93.9%) | 89.4(94.7%) |
| Comparative samples | | | |
| Activity of factor IX (%) | 120.2(100%) | 133.2(100%) | 94.4(100%) |

2.3 Testing a plurality of clotting factors before and after plasma is illuminated by using an automated coagulation analyzer: the results are shown in the following table 2-3.

TABLE 2-3

The impact on the activity of clotting factors of plasma by 60 minutes of circulatory processing

| Clotting factors (reduced) | Control plasma | processed plasma |
|---|---|---|
| PT | 14.9" (100%) | 19.6" (31.5%) |
| APTT | 63.0" (100%) | 74.0" (17.5%) |
| II | 24.6" (100%) | 25.0" (1.6%) |
| V | 29.2" (100%) | 31.8" (8.9%) |
| VII | 25.0" (100%) | 26.8" (7.2%) |
| VIII | 78.0" (100%) | 83.6" (7.2%) |
| IX | 63.6" (100%) | 66.7" (4.9%) |
| X | 29.6" (100%) | 32.6" (10.1%) |
| XI | 77.4" (100%) | 82.6" (6.7%) |
| XII | 67.7" (100%) | 70.2" (3.7%) |

2.4 Testing the impact on the content of complement $C_3$: is implemented by using a single-diffusion plate manufactured by Bangding Biological Corp. The operation conforms to the description from the manufacturer. Once the diameter of diffusive ring has been tested by using a vernier caliper, after a 48-hour diffusion, a corresponding content can be retrieved from a relevant content table. The results are shown as in the following table 2-4, which indicate the content of the complement $C_3$ of the plasma in whole blood source has reduced by about 5 percent after 60 minutes of circulatory processing if compared to a reference.

TABLE 2-4

The impact on the content of the complement $C_3$ of the plasma in whole blood source by 60 minutes of circulatory processing.

| Batch No. of samples | I | II | III |
|---|---|---|---|
| Processed samples (mg/ml) | 5.64 (95.1%) | 5.43 (93.7%) | 5.61 (95.9%) |
| Control samples (mg/ml) | 5.93 (100%) | 5.82 (100%) | 5.85 (100%) |

2.5 testing the impact on bio-chemical components such as plasma protein: is implemented by using an automatic bio-chemical analyzer. The testing results are shown in the table 2-5, 2-6, and 2-7.

TABLE 2-5

The impact on the activity of enzymes of the plasma in whole blood source by 60 minutes of circulatory processing.

| enzymes | unit | control plasma | processed plasma |
|---|---|---|---|
| GOT | iu/l | 19 (100%) | 16 (84.2%) |
| LDH | iu/l | 109 (100%) | 119 (109.2%) |
| CK | iu/l | 108 (100%) | 55 (50.9%) |
| AP | iu/l | 55 (100%) | 60 (109.1%) |
| GTE | iu/l | 16 (100%) | 17 (106.2%) |
| GPT | iu/l | 15 (100%) | 19 (126.6%) |

GOT (glutamic-pyruvic transaminase),
LDH (lactin dehydrogenase),
CK (Creatine Kinase),
AP (alkaline phosphatase),
GTE (glutamyl-transpeptidase endopeptidase),
GPT (Glutamic-pyruvic transaminase).

TABLE 2-6

The impact on the content of the plasma protein in whole blood source by 60 minutes of circulatory processing.

| enzymes | unit | control plasma | processed plasma |
|---|---|---|---|
| Glucose | mM/l | 22.6 (100%) | 21.2 (93.8%) |
| Total protein | g/l | 58.8 (100%) | 58.8 (100%) |
| Albumin | g/l | 36.8 (100%) | 36.1 (98.1%) |
| triglyceride | mM/l | 1.54 (100%) | 1.62 (105.2%) |

TABLE 2-7

The impact on the content of Inorganic Salt in whole blood source by 60 minutes of circulatory processing.

| Index name | unit | control plasma | processed plasma |
|---|---|---|---|
| Ca | mM/l | 1.40 (100%) | 1.57 (121.1%) |
| P | mM/l | 1.18 (100%) | 1.19 (100.8%) |
| Mg | mM/l | 0.66 (100%) | 0.67 (101.5%) |
| Na | mM/l | 135.7 (100%) | 135.1 (99.8%) |
| K | mM/l | 3.24 (100%) | 3.22 (99.3%) |
| Cl | mM/l | 58.9 (100%) | 58.7 (99.7%) |
| Cho | mM/l | 3.86 (100%) | 3.82 (98.9%) |

2.6 Testing the impact on the pH value of whole blood: is implemented by diluting the whole blood with 5 times of physiological saline and testing a variation on the pH values before and after the dilution by a Hanan pH meter. The results show (in Table 2-8) that the processing method of the present invention does not cause any change on the pH value of the whole blood itself.

TABLE 2-8

The impact on the pH value in whole blood by 60 minutes of circulatory processing.

| Batch No. of samples | I | II | III |
|---|---|---|---|
| Processed samples | 7.35 | 7.38 | 7.36 |
| Control samples | 7.34 | 7.38 | 7.36 |

2.7 Testing electrophoresis: includes implementing the tests of an immunoelectrophoresis, a crossed immunoelectrophoresis, a gel-electrophoresis, a SDS PAGE and an Western blot for the whole blood before the processing and for the whole blood after the processing respectively to verify no new antigen is generated; and testing the variation of electrophoresis band and the variation of electrophoresis mobility.

The above tests show that there are no apparent impacts on the physiological active compositions of plasma by a 60-minute circulatory processing by using the method of the present invention, on the condition of a complete illumination of virus.

3 Testing the adsorbent effect of methylene blue for the photosensitizer removing device:

In the present invention, a CAA is used as the adsorbent material for methylene blue. In order to test the adsorbent effects of the CAA for the methylene blue at different concentration in plasma, an absorbent device with a 2 cm filtering diameter is utilized, in which the CAA load is set to 7 cm high. A different amount of methylene blue may be added into plasma so that the final concentration of the plasma may be 1, 2, 3, 4, 6, 8, 10, 15, or 20 μmol/l. Respectively, absorbency tests are carried out to the plasma before the filtering and after the filtering. The results of the tests are shown in the table 3-1.

TABLE 3-1

Absorbency of CAA in the plasma by MB with different concentration

| MB concentration in plasma (μmol/l) | before filtering OD | after filtering OD | absorbency (%) |
|---|---|---|---|
| 1 | 0.063 | 0.001 | 98.4 |
| 2 | 0.114 | 0.003 | 97.4 |
| 3 | 0.173 | 0.009 | 94.8 |
| 4 | 0.227 | 0.020 | 91.2 |
| 6 | 0.340 | 0.027 | 92.1 |
| 8 | 0.447 | 0.038 | 91.5 |
| 10 | 0.560 | 0.044 | 92.2 |
| 15 | 0.805 | 0.054 | 93.3 |
| 20 | 1.043 | 0.069 | 93.4 |

A test to methylene blue content is done after the whole blood source is received 60 minutes of circulatory processing by using the present invention. The result of the test shows the concentration of methylene blue is 0.002 μmol/l. It proofs that the MB added in the plasma has been absorbed after the plasma flows through the device for removing photosensitizer.

According to the above tests, the present invention is proofed to have an apparent effect on illumination of virus but a small impact on other biological indices of the blood. A purified blood can be obtained after processed by its method; The device for removing photosensitizer absorbs the added photosensitizer, thereby maximally reducing the possible side effects of the photosensitizer onto human body; in addition, since the present invention utilizes a disposable sealed system isolated from the outside environment to deal with whole blood, an occurrence of re-infection of the blood is reduced and the operational procedure is simplified at the same time; Consequently, blood processing can be implemented in a batch, as a pipeline, during blood circulation so that a real-time online illumination of virus is realized to the blood and the safety of the blood is guaranteed.

Simulation 1:

A simulation of extracorporeal circulation is conducted to observe the decreasing speed of virus titer in human blood circulation due to the present illumination technology. A 1500 ml of plasma, which contains the model virus, from healthy human being is first put in a closed storage bank; under the operational force of a peristaltic pump, the plasma flows and forms a circulatory path. When the flowing speed of the blood is set to 50 ml/min, in order to test the decrease of virus titer of VSV and Sindbis in the plasma, different times for circulation are set to illuminate the virus. The results show both kinds of viruses have reduced by over 5.0 Lg $TCID_{50}$ (refer to Table 4).

TABLE 4

The decreasing speed of virus titer in plasma storage bank.

| Illumination | residual virus (Lg $TCID_{50}$) | |
|---|---|---|
| time (h) | VSV | Sindbis |
| 1 | 2.63 | 2.88 |
| 2 | −0.13 | 0.37 |
| 4 | ≤−0.50 | <−0.50 |
| Control | 5.25 | 5.50 |

\* The total volume of the plasma storage bank is 1500 ml; the flowing speed of the plasma is 50 ml/min; The processed plasma is illuminated in a standard blood bag with three pressed folded lines and a length of 15 cm.

Simulation 2:

Simulation 2 is to observe how the shape of blood bag and plasma flowing speed influence the effect of illumination of virus in a simulated extracorporeal circulation. Since the standard blood bag causes the plasma flowing through at shorter time, a better effect of illumination of virus is hard to reach, so in the simulation, the standard blood bag is modified. The results show the effect of illumination of virus is significantly improved (See Table 5) by using a blood bag with five pressed folded lines to process a plasma flowing at 50 ml/min.

Simulation 3:

Simulation 3 experiments how the length of an illumination path makes impact on illumination of virus in a simulated extracorporeal circulation. In order to prolong the illuminating time of the light source for illuminating the flowing plasma and enhance the effect of illumination of virus, a study of using a PVC photic transfusion tube with an alternative length to replace the blood bag is conducted to observe how the length of the illumination path makes impact on illumination of virus. When the length of the illumination path is set to 2 meter, the illumination time is set to 26 seconds and the flow speed of the plasma is set to 50 ml/min, more than 5 Lg$TCID_{50}$ of VSV and Sindbis virus can be illuminated (see table 6).

TABLE 5

Impact on the effect of illumination of virus by shape of blood bag and plasma flowing speed

| Shape of blood bag | plasma flowing speed (ml/min) | virus titer left (VSV, Lg $TCID_{50}$) |
|---|---|---|
| A standard 15 cm cut-through plasma bag | 50 | 4.25 |
| | 80 | 5.13 |
| | | 6.25 (control) |

TABLE 5-continued

Impact on the effect of illumination of virus by shape of blood bag and plasma flowing speed

| Shape of blood bag | plasma flowing speed (ml/min) | virus titer left (VSV, Lg $TCID_{50}$) |
|---|---|---|
| A standard 15 cm (with three pressed folded lines in the middle) | 50 | −0.25 |
| | 80 | 1.50 |
| | | 5.25 (control) |
| A standard 15 cm (with five pressed folded lines in the middle) | 50 | ≤−0.50 |
| | 80 | 0.13 |
| | | 4.63 (control) |

TABLE 6

Impact on the effect of illumination of virus by the length of illumination path

| Length of illumination path (m) | illumination time (sec) | virus liter left (Lg $TCID_{50}$) | |
|---|---|---|---|
| | | VSV | Sindbis |
| 4.0 | 52.0 | ≤−0.5 | ≤−0.5 |
| 3.5 | 45.5 | ≤−0.5 | ≤−0.5 |
| 3.0 | 39.0 | ≤−0.5 | ≤−0.5 |
| 2.5 | 32.5 | ≤−0.5 | ≤−0.5 |
| 2.0 | 26.0 | ≤−0.5 | ≤−0.5 |
| control | | 6.0 | 5.3 |

Annotation: the flowing speed of the plasma is 50 ml/min.

The invention claimed is:

1. A method for reducing the virus load from a whole blood sample, comprising:
   (a) removing an amount of whole blood from a patient, a blood bag, or a blood storage device, wherein the removed whole blood contains at least one virus selected from the group consisting of Sindbis virus (SINV) and vesicular stomatitis virus (VSV);
   (b) adding a sufficient amount of an anticoagulant to the removed whole blood;
   (c) centrifugally separating the anticoagulated whole blood into a plasma fraction containing said at least one virus and a red blood cell containing fraction;
   (d) performing a light treatment on the separated plasma fraction, comprising:
      (i) mixing a photosensitizer methylene blue with the separated plasma fraction by means of a peristaltic pump to enable an interaction between the photosensitizer methylene blue and the at least one virus present in the separated plasma fraction; illuminating the photosensitizer methylene blue-plasma mixture with a 600-700 nm wavelength LED for 60 seconds; and filtering the photosensitizer methylene blue and virus from the plasma mixture by passing the photosensitizer methylene blue-plasma mixture illuminated from step (d)(ii) through a filter comprising attapulgite, thereby providing a light-treated plasma;
   (e) mixing the light-treated plasma from step (d)(iii) with the separated red blood cell containing fraction from step (c) to form a reconstituted whole blood; and
   (f) transfusing the reconstituted whole blood into the patient, blood bag, or blood storage device,
   wherein the sequence of steps (c) to (e) are performed once or multiple times prior to the transfusing of step (f), and wherein, once sufficient treated reconstituted whole blood is obtained, the whole blood is simultaneously removed from the patient, blood bag, or blood storage device through a first tube while treated reconstituted whole blood is transfused back into the patient, blood bag, or blood storage device through a second tube.

2. The method of claim 1, wherein the whole blood is freshly isolated whole blood obtained from said patient.

3. The method of claim 1, wherein the at least one virus is Sindbis virus.

4. The method of claim 1, is repeated until the viral load in the reconstituted whole blood system is reduced by 99.99% relative to the viral load in the initial sample of the whole blood removed from the patient, blood bag, or blood storage device.

5. The method of claim 1, wherein the removing of the whole blood of step (a) is at a rate of 30 to 150 ml per minute.

6. The method of claim 1, wherein the removing of the whole blood of step (a) occurs at the same rate as the transfusing of the reconstituted whole blood of step (f).

7. The method of claim 1, wherein steps (a)-(f) are performed in an aseptic, sealed system which isolates the system from the outside environment.

8. The method of claim 1, wherein in step (d)(i) the mixing of the photosensitizer methylene blue with the separated plasma fraction by said peristaltic pump comprises (a) transferring a volume of the photosensitizer at a first rate and (b) transferring a volume of the separated plasma fraction at a second rate, wherein the first rate is 1% of the second rate.

* * * * *